United States Patent

Snyder et al.

Patent Number: 5,918,272
Date of Patent: Jun. 29, 1999

[54] MAGNETIC AND ULTRASONIC DISCRIMINATOR FOR PARTICLE SIZE DISTRIBUTION ANALYZER

[75] Inventors: Dane Thomas Snyder, Byron; Robert James Law; Michel Noel Robles, both of Livermore; Roger William Caputi, Walnut Creek, all of Calif.

[73] Assignee: General Electric Company, San Jose, Calif.

[21] Appl. No.: 08/631,492

[22] Filed: Apr. 12, 1996

[51] Int. Cl.[6] ............................. B01D 35/06; B03C 1/02; B03C 1/30; C02F 1/48
[52] U.S. Cl. ...................... 73/61.42; 73/53.07; 73/61.72; 73/865.5; 210/222; 210/695; 324/204
[58] Field of Search .................................. 73/53.07, 61.41, 73/61.42, 61.71, 61.72, 61.75, 64.53, 865.5, 865.8; 95/28; 210/222, 223, 294, 295, 333.01, 695; 324/204

[56] References Cited

U.S. PATENT DOCUMENTS

| | | | |
|---|---|---|---|
| 2,188,516 | 1/1940 | Payne | 210/222 |
| 3,433,057 | 3/1969 | Halsey | 73/61.41 X |
| 4,909,081 | 3/1990 | Kulczyk et al. | 73/61.75 X |
| 5,061,364 | 10/1991 | Metala et al. | 73/53.07 X |
| 5,540,089 | 7/1996 | Fitch | 73/61.72 X |
| 5,708,198 | 1/1998 | Fitch et al. | 73/61.42 |

FOREIGN PATENT DOCUMENTS 3-110446  5/1991  Japan ..................... 73/61.42

*Primary Examiner*—Hezron Williams
*Assistant Examiner*—Daniel S. Larkin
*Attorney, Agent, or Firm*—James E. McGinness; Dennis M. Flaherty

[57] ABSTRACT

A flow-through system for determining the particle size distribution of iron oxide particulate matter in a reactor water sample. The system includes a magnetic filter having a chamber through which a stream of reactor water. The chamber is surrounded by a winding which is coupled to an electrical circuit for generating a varying magnetic field which interacts with any magnetic particulates entrained in the water sample flowing through chamber. When a strong magnetic field is established, magnetic particles are filtered out of the water stream flowing through the chamber by magnetic attraction. Therefore, only particles which are non-magnetic or slightly magnetic pass through the magnetic filter. The particles which pass through the magnetic filter then enter a conventional particle distribution analyzer which counts and sizes the particles in the water stream flowing therethrough.

11 Claims, 1 Drawing Sheet

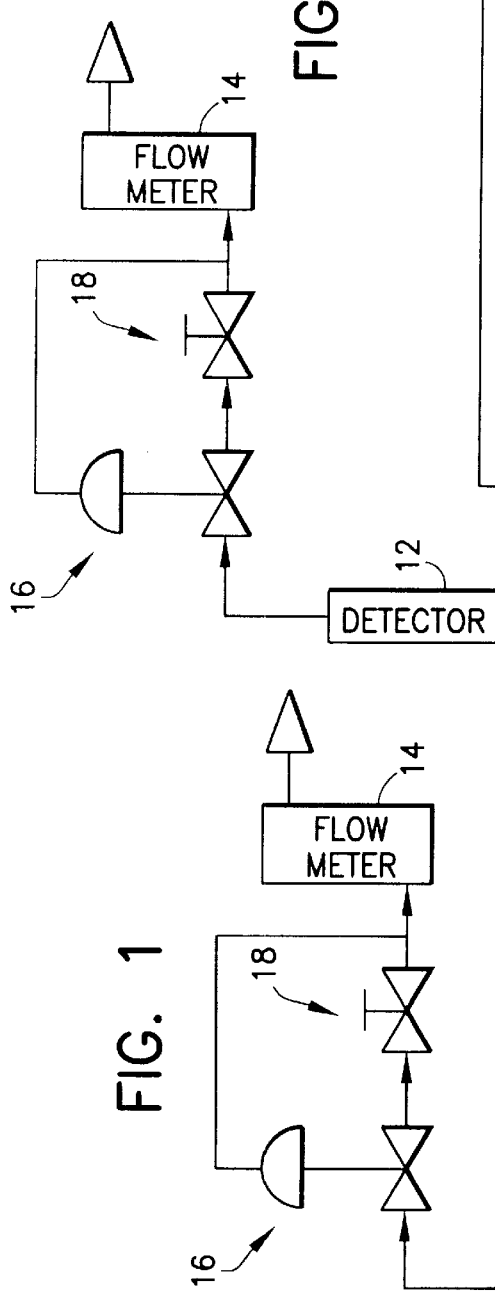
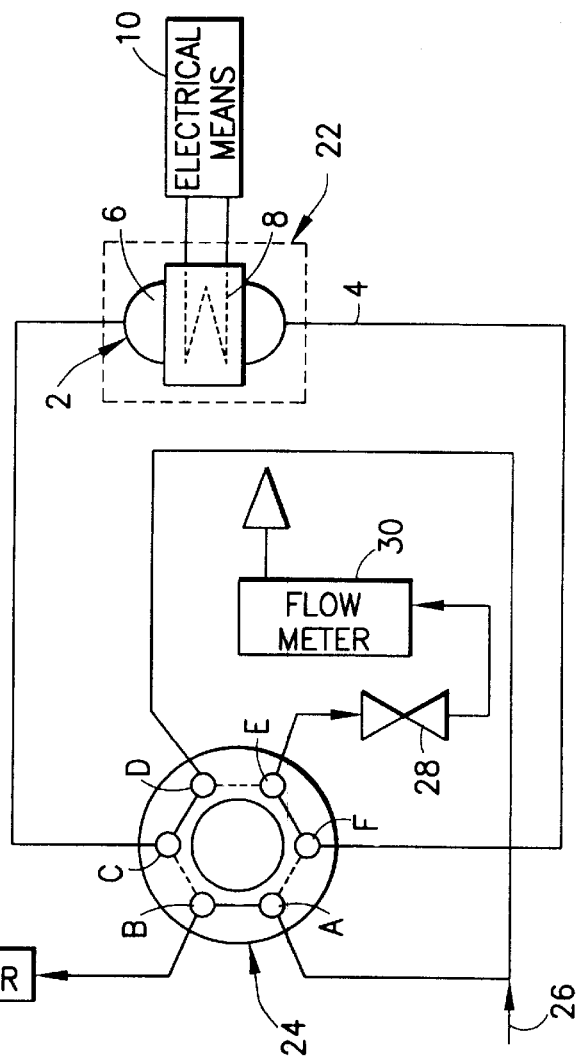
FIG. 1
FIG. 2

MAGNETIC AND ULTRASONIC DISCRIMINATOR FOR PARTICLE SIZE DISTRIBUTION ANALYZER

FIELD OF THE INVENTION

This invention generally relates to the operation and safety of water-cooled nuclear reactors. In particular, the invention relates to methods for minimizing the risk of exposure of workers to radioactive emissions during reactor shutdown for refueling and/or maintenance.

BACKGROUND OF THE INVENTION

The presence of iron oxides as particulate matter in the coolant water of boiling water reactor (BWR) plants has adverse effects on the plant operating characteristics. High concentrations of iron input are known to cause heat transfer problems with the fuel. Also, the activation and transport of Co-60 isotope is related to the iron concentration in the reactor water.

A major hazard in water-cooled nuclear reactors is the accumulation of radioactive substances in the structural portions of the reactor. The buildup of radioactive nuclides occurs on the inner surfaces of components which are in contact with the reactor water. This includes both the primary recirculation circuit and the reactor water cleanup system. During reactor shutdown, workers are exposed to radiation emanating from stainless steel internal walls and inner surfaces of piping. Radioactive materials retained in oxide films which have accumulated on wall and piping surfaces are a major source of radiation exposure. The radioactivity has been found to be predominantly due to the Co-60 isotope. As a result, a substantial effort has been made to identify the key parameters which affect Co-60 buildup and to determine and implement methods for limiting that buildup.

The radiation buildup, controlled mainly by the Co-60 isotope concentration, occurs by two processes. First, the Co-60 isotope which is dissolved in the reactor water incorporates into the crystalline structure of the oxide film as the latter is formed on the stainless steel surfaces. Second, the Co-60 isotope sorbs onto the surfaces of particulates, such as iron oxides, floating in the reactor water or on the fuel. Iron oxide particles which contain sorbed Co-60 isotope tend to deposit in regions of relatively low water flow velocity. This leads to regions of higher radioactivity which are commonly referred to as "hot spots".

The use of very dilute (trace) concentrations of zinc oxide in the reactor water has been demonstrated, both in the laboratory and in boiling water reactors, to limit the incorporation of $^{60}Co$ into the oxide film. Because naturally occurring zinc contains $^{64}Zn$ isotope which is converted to radioactive $^{65}Zn$ in a nuclear reactor, the $^{64}Zn$ is removed during the manufacturing process. Zinc from which the $^{64}Zn$ isotope has been substantially removed is referred to as "depleted zinc".

The adverse effect of iron oxide particulate matter in the reactor coolant is amplified by the use of depleted zinc to reduce the uptake of Co-60 on out-of-core piping surfaces. A high concentration of iron requires an increase in the amount of depleted zinc injected and a concomitant increase in cost. Hence, it is desirable to develop a technique to reduce particulate iron in the BWR coolant. Understanding the form and nature of particulate iron at the various types of plants is very important information when considering solutions to mitigate the problem.

The major iron oxide forms found in BWR coolant are magnetite ($Fe_3O_4$) and hematite ($Fe_2O_3$), which are magnetic species, and α—FeOOH and γ—FeOOH, which are non-magnetic species. This determination is conventionally made by accumulating particulate samples on filter membranes and doing a laboratory analysis for crystal structure by X-ray diffraction. The size distribution of each species has been difficult to determine, even using scanning electron microscopy (SEM). There has also been a serious concern that the collected material may change form during transport to the analytical laboratory.

Thus, there is a need for a particle sizing system which measures the distribution of particles in a flowing water stream in a relatively short time period (a few minutes). This information is useful in the design of filters for removing the particulate matter as well as for identifying the source of the particulate matter.

SUMMARY OF THE INVENTION

The present invention is a method and an apparatus for overcoming the aforementioned problems. The apparatus was designed to enhance the ability of the particle distribution analyzer to discriminate between iron oxide forms using magnetic and ultrasonic fields. The device is a water conduit configured such that a magnetic field and ultrasonic waves are produced (or eliminated) to interact with particulates in the water. When a strong magnetic field is established, magnetic particles collect from the flowing stream in this device. Therefore, only particles of little or no magnetic qualities pass on through to the sensor cell in a particle sizing and counting system.

The strength of the magnetic field is varied, making it possible to discriminate particles magnetically. This function is very important in BWR chemistry because the two major insoluble constituents in the coolant are magnetite, which is strongly magnetic, and hematite, which is paramagnetic (weakly magnetic).

The particulate bonding and/or agglomeration characteristics are defined by subjecting the liquid stream to ultrasonic waves. The degree of bonding is determined as a function of intensity of the ultrasonics, using the resulting change in particle size distribution as the confirming measurement. The volume of the sample must be known for proper quantification by discrimination.

BRIEF DESCRIPTION OF THE DRAWINGS

FIG. 1 is a block diagram showing the flow path of reactor water in a flow-through particle sizing and counting system in accordance with one preferred embodiment of the invention.

FIG. 2 is a block diagram showing the flow path of reactor water in a particle sizing and counting system having backflush and reference flow features in accordance with another preferred embodiment of the invention.

DETAILED DESCRIPTION OF THE PREFERRED EMBODIMENTS

In accordance with one preferred embodiment (shown in FIG. 1), a flow-through system for determining the particle size distribution of iron oxide particulate matter in a reactor water sample comprises a magnetic filter 2 having a sample inlet 4 for receiving a stream of reactor water. The magnetic filter comprises a chamber 6 surrounded by a winding 8 and electrical means 10 coupled to winding 8 for generating a varying magnetic field which interacts with any magnetic particulates entrained in the water sample flowing through chamber 6. When a strong magnetic field is established, magnetic particles are collected from the water stream flowing through the chamber 6 by magnetic attraction. Therefore, only particles which are non-magnetic or slightly magnetic pass through the magnetic filter 2.

The particles which pass through the magnetic filter then enter a detector 12. The detector 12 is a conventional particle distribution analyzer comprising multi-channel optical means for counting and sizing the particles in the water stream flowing therethrough.

The water stream exiting the detector 12 flows into a conventional flowmeter 14 via a constant downstream pressure controller 16 and a manually operated flow control valve 18. The flow control valve 18 is used to provide constant flow control. The pressure controller 16 mechanically maintains a constant pressure across valve 18. If the valve is fully open, the flow will be high. If the valve is nearly closed, the flow will be low. If the pressure controller works and the valve does not plug, the flow will be constant. If the water flowing through the valve has a high particulate content, a feedback from a flow monitor can be used to adjust the valve. It is important to control flow (to a known volume) to enable quantification and discrimination of particles.

The data acquired by the particle distribution analyzer is compiled and processed to determine the particle size distribution in each sample of reactor water. The analytical strategy is to first obtain the particle distribution in the absence of any discriminating mechanism, i.e., with the magnetic filter 2 turned off. The sample stream is then exposed to a magnetic field which is tuned to attract and thereby collect magnetite but not hematite. Then the size distribution of the particles remaining in the through-flow is determined. The amount and size distribution of magnetite are determined by subtracting the results of the second measurement from the first measurement.

The hematite is characterized in a similar manner by increasing the intensity of the magnetic field so that magnetite and hematite are attracted and collected by the magnetic filter, leaving only the non-magnetic iron oxide species in the sample stream which enters the detector 12. Then the size distribution of the non-magnetic particles is determined. The amount and size distribution of hematite is determined by subtracting the results of the third measurement from the second measurement. The particle size distribution of the non-magnetic iron oxides is information that has not been available using conventional methods.

In accordance with a further aspect of the invention, the particulate bonding and/or agglomeration characteristics are determined by subjecting the sample stream to ultrasonic waves. This is accomplished using an ultrasonic generator 22 comprising (in conventional fashion) a pulser circuit, a transmitter circuit, and a piezoelectric transducer acoustically coupled to the sample stream flowing through the magnetic filter chamber. Ultrasonic waves are transmitted into the discriminating cell for two purposes. The first purpose is to disperse the magnetic particles after the magnetic field is removed. The second purpose is to use the ultrasonic wave intensity to discriminate the degree of bonding. The degree of bonding of sub-particles in forming larger particles is determined as a function of amplitude of the ultrasonic waves, using the resulting change in particle size distribution as the confirming measurement.

In accordance with an alternative preferred embodiment of the invention shown in FIG. 2, the system has backflush and reference flow features. The backflush feature provides automatic cleaning of the magnetic filter and its associated plumbing. The reference flow feature provides a convenient and automatic data reference to determine any bias or drift caused by the magnetic filter module in its unpowered state. An example of this type of problem is particle build-up in the module because of a gradual increase in residual magnetic fields induced in the hardware. The inclusion of means for degaussing (i.e., removing or reversing the magnetic field), triggered during the backflush mode, eliminates this problem. It is during the backflush mode that data from the reference flow is acquired.

Referring to FIG. 2, the system with backflush and reference flow features comprises a six-port switching valve 24 having two ports A and D connected to a sample inlet 26; a port B connected to the inlet of the detector 12; a port C connected to the outlet of the magnetic filter chamber 6; port E connected to a backflush flow control valve 28; and port F connected to the inlet of magnetic filter chamber 6. The backflush flow control valve 28 is in turn connected to the input of a flowmeter 30, which measures the flow through the magnetic filter during backflushing.

In the backflush mode, valve 24 is switched so that port A communicates with port B; port C communicates with port D; and port E communicates with port F. When a fluid is injected at sample inlet 26, a reference portion of the fluid flows into the detector 12 via ports A and B. The detector counts and sizes any particles entrained in this reference flow. The other part of the injected fluid flows through ports D and C and then backflushes the magnetic filter chamber 6, entering the chamber via its outlet and exiting the chamber via its inlet. The backflushing fluid then enters the flowmeter 30 via ports F and E and backflush flow control valve 28. The foregoing connections between ports A and B, C and D, and E and F are indicated by solid lines in FIG. 2.

When the valve 24 is in the "reference" position, the particles detected do not pass through the discrimination device. Therefore the measurement is the true (actual) distribution of particles that can be used as a reference. Switching the valve diverts the water through the discriminator. If the discriminator were not backflushed clean of particles, the sample would be biased by residual particles, thereby giving a false reading. The system shown in FIG. 1 will give a biased reading when the magnetic field is removed and the ultrasonic field is applied. This occurs because the retained particles are discharged through the detector for a finite period of time. This problem can be quantified and eliminated in the second system depicted in FIG. 2.

To magnetically discriminate particles as previously described with reference to the flow-through system of FIG. 1, the six-port switching valve 24 is switched so that port A communicates with port F and port C communicates with port B. When a fluid sample is injected at sample inlet 26, the sample flows through ports A and F; into the magnetic filter chamber 6 via inlet 4; through the magnetic filter chamber; through ports C and B; and into the detector 12. The detector then counts and sizes any particles entrained in this fluid sample, as previously described.

The foregoing preferred embodiments have been disclosed for the purpose of illustration. Variations and modifications of the disclosed apparatus will be readily apparent to practitioners skilled in the art of particle distribution analysis. All such variations and modifications are intended to be encompassed by the claims set forth hereinafter.

What is claimed is:

1. A magnetic filter for separating particulate matter, comprising:

a flow-through chamber having an inlet and an outlet;

means for supplying a fluid to said inlet of said flow-through chamber;

a winding wound around said flow-through chamber; and electrical means coupled to said winding for generating a varying magnetic field which attracts and collects in said flow-through chamber particles having a predetermined magnetic property entrained in said fluid flowing through said flow-through chamber.

2. The magnetic filter as defined in claim 1, further comprising an ultrasonic generator acoustically coupled to transmit ultrasonic waves into fluid inside said chamber.

3. A system for determining the size distribution of particles entrained in a fluid, comprising:

a flow-through chamber having an inlet and an outlet;

means for supplying a fluid to said inlet of said flow-through chamber;

a winding wound around said flow-through chamber; and electrical means coupled to said winding for generating a varying magnetic field which attracts and collects in said flow-through chamber particles having a predetermined magnetic property entrained in the fluid flowing through said flow-through chamber; and a particle size distribution detector connected to said outlet of said flow-through chamber for receiving fluid having particles entrained therein, said entrained particles not having said predetermined magnetic property.

4. The system as defined in claim 3, wherein said particle size distribution detector comprises means for optically counting and sizing particulate matter in a stream flowing through said detector.

5. The system as defined in claim 3, further comprising an ultrasonic generator acoustically coupled to transmit ultrasonic waves into fluid inside said chamber.

6. A system for determining the size distribution of particles entrained in a fluid, comprising:

a flow-through chamber having an inlet and an outlet;

means for generating a magnetic field which attracts and collects particles having a predetermined magnetic property entrained in a fluid flowing through said flow-through chamber; and a particle size distribution detector connected to said outlet of said flow-through chamber; and switching valve means having a first switched state wherein a sample inlet is in fluid communication with an inlet of said particle size distribution detector and with said outlet of said chamber so that fluid injected into said sample inlet backflushes said chamber, and a second switched state wherein said sample inlet is in fluid communication with said inlet of said chamber, and said outlet of said chamber is in fluid communication with said inlet of said detector.

7. The system as defined in claim 6, wherein said switching valve means comprises a six-port switching valve having a first port connected to said inlet of said chamber, a second port connected to said outlet of said chamber, third and fourth ports connected to said sample inlet, and a fifth port connected to said inlet of said detector.

8. A method for determining particle size distributions for first and second species of particulate matter entrained in a fluid when said fluid also has particulate matter entrained therein other than said first and second species, wherein said first and second species of particulate matter are magnetic, but said second species is less magnetic than said first species, comprising the steps of:

causing a first sample of said fluid to flow through a particle size distribution analyzer;

using said particle size distribution analyzer to acquire a first particle size distribution of the particulate matter in said first sample;

causing a second sample of said fluid to flow through a chamber;

applying a magnetic force of attraction to said second sample of flowing fluid sufficient to filter said particulate matter of said first species from said flowing fluid;

causing said filtered second sample to flow through said particle size distribution analyzer;

using said particle size distribution analyzer to acquire a second particle size distribution of the particulate matter in said filtered second sample;

determining a particle size distribution of the particulate matter of said first species in said fluid by subtracting said second particle size distribution from said first particle size distribution;

causing a third sample of said fluid to flow through said chamber;

applying a magnetic force of attraction to said second sample of flowing fluid sufficient to filter said particulate matter of said first and second species from said flowing fluid;

causing said filtered third sample to flow through said particle size distribution analyzer;

using said particle size distribution analyzer to acquire a third particle size distribution of the particulate matter in said filtered third sample; and determining a particle size distribution of the particulate matter of said second species in said fluid by subtracting said third particle size distribution from said second particle size distribution.

9. The method as defined in claim 8, wherein said first species is magnetite, said second species is hematite and said particulate matter other than said first and second species includes iron oxides.

10. A method for determining a particle size distribution for a first species of particulate matter entrained in a fluid when said fluid also has particulate matter entrained therein other than said first species, wherein said first species of particulate matter is magnetic, comprising the steps of:

causing a first sample of said fluid to flow through a particle size distribution analyzer;

using said particle size distribution analyzer to acquire a first particle size distribution of the particulate matter in said first sample;

causing a second sample of said fluid to flow through a chamber;

applying a magnetic force of attraction to said second sample of flowing fluid sufficient to filter said particulate matter of said first species from said flowing fluid;

causing said filtered second sample to flow through said particle size distribution analyzer;

using said particle size distribution analyzer to acquire a second particle size distribution of the particulate matter in said filtered second sample;

determining a particle size distribution of the particulate matter of said first species in said fluid by subtracting said second particle size distribution from said first particle size distribution; and coupling ultrasonic waves into said chamber.

11. The method as defined in claim 10, wherein said step of coupling ultrasonic waves into said chamber is performed after the magnetic field is turned off, the amplitude of said ultrasonic waves being sufficient to disperse magnetic particulate matter lodged in said chamber.

* * * * *